(12) United States Patent  
Mohl

(10) Patent No.: US 6,506,146 B1
(45) Date of Patent: Jan. 14, 2003

(54) APPARATUS FOR SUPPORTING HEART PERFORMANCE

(76) Inventor: Werner Mohl, Hafnerberg 66, A-2571 Altenmarkt/Thennenberg (AT)

( * ) Notice: Subject to any disclaimer, the term of this patent is extended or adjusted under 35 U.S.C. 154(b) by 0 days.

(21) Appl. No.: 09/509,077

(22) PCT Filed: Sep. 17, 1998

(86) PCT No.: PCT/AT98/00225
§ 371 (c)(1),
(2), (4) Date: May 12, 2000

(87) PCT Pub. No.: WO99/15213
PCT Pub. Date: Apr. 1, 1999

(30) Foreign Application Priority Data

Sep. 22, 1997 (AU) .............................................. 1800/97

(51) Int. Cl.⁷ ............................................... A61N 1/362
(52) U.S. Cl. ........................... 600/17; 600/508; 600/526
(58) Field of Search ............................. 600/10–18, 508, 600/526; 604/6.11, 8–10, 540

(56) References Cited

U.S. PATENT DOCUMENTS 4,674,518 A   6/1987   Salo
5,308,319 A   5/1994   Ide et al.
5,449,342 A   9/1995   Hirose et al.

FOREIGN PATENT DOCUMENTS

| EP | 0 075 606 A | 4/1983 |
| EP | 0 075 606 | 4/1983 |
| EP | 0 503 839 A2 | 9/1992 |
| EP | 0 503 839 A | 9/1992 |
| FR | 1 187 249 A | 8/1959 |
| FR | 1.1987.249 | 9/1959 |

*Primary Examiner*—Mark Bockelman
(74) *Attorney, Agent, or Firm*—Nixon & Vanderhye P.C.

(57) ABSTRACT

In a means for support of the performance of a heart (1) in which fluid is taken from blood vessels via an external pump (7) and is returned to the blood vessels, the amount of fluid being controlled as a function of the measured values, a catheter in the ventricle is equipped with sensors (4) for measuring the volume of fluid per unit of time. The sensors (4) are connected to an evaluation circuit in which the ratio of the diastolic volume to the systolic volume per heartbeat or unit of time, especially the output rate and/or the deviation of the volume which has been delivered by the heart per unit of time from a defined setpoint, for example the setpoint which has been computed from body-specific data for the cardiac output (HZV), is evaluated and a signal is generated. The pump (7) via which fluid is withdrawn from the ventricle is controlled depending on the generated signal.

14 Claims, 1 Drawing Sheet

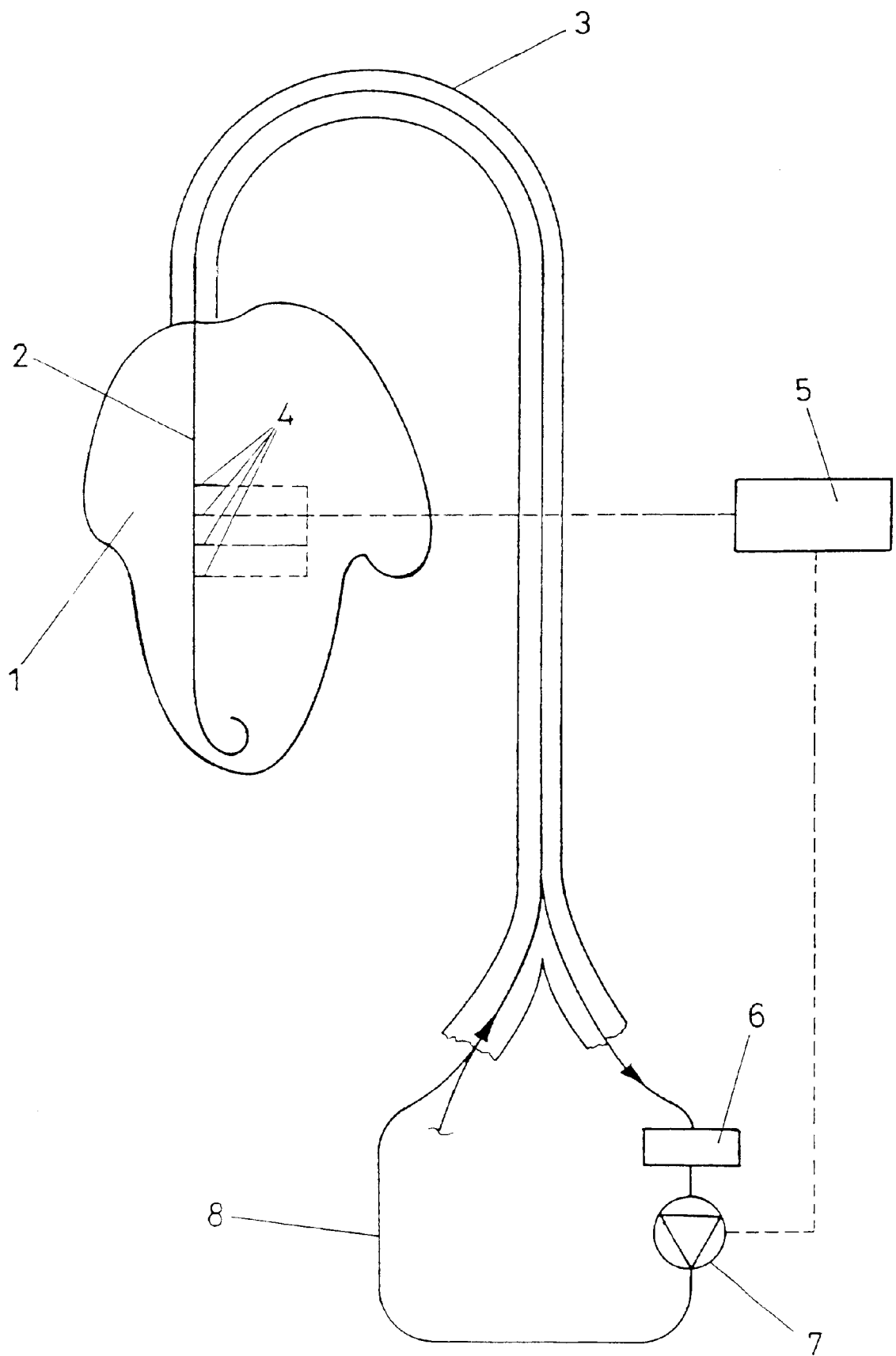

APPARATUS FOR SUPPORTING HEART PERFORMANCE

BACKGROUND OF THE INVENTION

The invention relates to an apparatus for supporting performance of the heart in which fluid is taken from blood vessels via a suction catheter and a suction means, and is returned to the blood vessels via a return catheter, the amount of fluid being controlled as a function of measured values.

BRIEF DESCRIPTION OF THE INVENTION

After heart failure, especially a cardiac infarction or other event that causes a decrease in heart performance, it is important for intensive medicine to normalize and stabilize cardiac function again as quickly as possible. Especially when, for example, the volumetric performance of the heart is clearly reduced as a result of failure, the intention is to reliably and promptly restore corresponding peripheral circulation in order to prevent secondary damage. Use of heart-lung machines in principle allows important liver functions to be maintained. But special adaptation to the specific requirements at the time is generally not done with such machines. Rather, conventional heart-lung machines merely maintain forced blood circulation using external pumps without deliberately understanding the respective requirements of the weakened or failed heart.

In surgery, especially in the area of the veins, it has already been suggested that retroinfusion controlled by venous pressure out of or into the veins of the body be done with the suction of fluid and return of the fluid via a pump. Here conventional catheters are used with lumina which allow fluid suction and via which lumina return is enabled at a suitable location. Known means, especially for retroinfusion of blood in coronary veins in the area of myocardial protection during a brief closure of the coronary arteries within the framework of heart surgery, are generally undertaken such that the balloon dilation of a coronary artery narrowed by arteriosclerosis is done. In these cases, compensation which has been adapted to the brief intervention can be done by return of the suctioned blood into the veins. For continuous restitution of complete function of a heart however, those criteria cannot be considered which would be relevant for complete function of the heart and therefore there is no intensive supply over a certain time interval with these means. At the same time, the supply to the other organs must be maintained.

The object of the invention is to devise a modular means with which the respective requirements of all organ systems during intensive treatment of a damaged hart using conventional and tested components can be taken into account. To achieve this object, the means as claimed in the invention consists essentially in that there is at least one sensor which allows measurement of the volume of fluid per unit of time or determination of measured quantities which are proportional to the volume, and the sensor(s) is (are) connected to an evaluation circuit in which the ratio of the diastolic volume to the systolic volume per heartbeat or unit of time, especially the output rate and/or the deviation of the volume which has been delivered by the art per unit of time from a defined setpoint, for example the setpoint which has been computed from body-specific data for the cardiac output (HZV), is evaluated and a signal is generated the suction means is controlled depending on the generated signal. Catheters for intraventricular acquisition of the chamber volume are known. Conventionally, with these catheters which are inserted into the ventricle, an electrical field is generated at a host of sites and the conductivity is measured. Conclusions regarding the ventricle volume can be drawn from the measured values. Because at this point one such volume measurement is evaluated to the extent that the cardiac performance is checked, and especially the so-called output rate or the cardiac output is determined, it becomes possible to achieve optimization to the extent that a signal is generated with which a suction means can be controlled such that it in fact yields the additional necessary performance and, at the same time, reduces the volume remaining in the ventricle at each beat accordingly. Overall, with the means as claimed in the invention, the focus is on improvement of the output rate and thus improvement of the cardiac performance, and the use of measured values for the diastolic and systolic volume here for selective adaptation to the respective optimal attainable reduction of the interior volume of the heart can be represented and used for the required cardiac performance. The suction means thus should in principle replace that performance which cannot yet be furnished initially by the damaged heart, whereupon further measures can raise the cardiac performance accordingly to the normal amount. Preferably, the suction catheter is equipped with at least one sensor for volume measurement, preferably the suction catheter being made as a cardiac ventricle catheter. The suction means can be made as a controllable external pump in an especially simple way.

Advantageously, the design as claimed in the invention is made such that the control of the external suction means is connected such that the delivery performance of the external suction means is increased at a low output rate and at low delivery performance of the heart, and is reduced at correspondingly higher measured values. The delivery performance of the suction means or the pump is thus controlled primarily such that overall an output rate which corresponds to a healthy heart is simulated. The suction means can be operated, especially cycled, by which in the blood vessels, the corresponding pulse signals are also formed which contribute to normalization of the pulse frequency and cardiac performance. Advantageously, the design is made here such that the delivery performance of the of the external suction means or pump is controlled preferentially as a function of the measured values for the output rate up to achieving an output rate between 65 and 80%.

In addition to the output rate as a measure for the required correction measures and especially as a control signal for the performance of the external suction means or pump, advantageously a setpoint which has been computed from body-specific data can be used for the cardiac output as a measured quantity. Further adaptation and shortening of the interval until normalization of the suction performance of a heart can thus be achieved by the suction performance of the external suction means being undertaken depending on the computed and the measured cardiac output, such that the external suction means delivers the difference between the computed cardiac output and the measured value per unit of time.

In principle, as already mentioned, the suction means can preferably be controlled as a discontinuously cycled pump, by which better adaptation to the desired pulse frequency is achieved. In particular, it can be advantageous here to fix the cycle of the external suction means. In the case of tachycardia, one such fixed cycle frequency of the external suction means can however lead to undesired interference with the heart rate so that advantageously, the procedure is such that the suction means is synchronized to the heartbeat.

In the case of tachycardia, the cycle of the suction means is reduced relative to the heartbeat in a defined ratio.

In order to ensure the correspondingly cycled return of the fluid, in addition to the measure of operating the external suction means discontinuously, in addition or alternatively also cycled perfusion with a catheter which occludes on a cycled basis can be done. Advantageously, the means as claimed in the invention can be operated such that return of the fluid by adjusting the cycle of the suction means of the discontinuously delivering suction means or by (cycled) perfusion with a catheter which occludes on a cycled basis takes place during the diastole, in the latter case optionally one continuously conveying external suction means or pump being used.

The blood is returned preferably in turn to an arterial vessel and at a suitable location near the point at which the blood was removed. In this way, it is ensured that circulation through all vessels is as uniform as possible is guaranteed.

A further improvement using the modularly built system arises when the process is such that blood from the right heart or large veins is removed volumetrically, enriched with $O_2$ in a oxygen generator and pumped in the circulation.

The means as claimed in the invention is detailed schematically using the drawings.

BRIEF DESCRIPTION OF THE DRAWINGS

FIG. 1 is a schematic diagram illustrating the apparatus of this invention in association with the heart of a patient.

DETAILED DESCRIPTION OF THE INVENTION

FIG. 1 illustrates in generally schematic form the heart 1 into which a cardiac ventricle catheter 2 is inserted. The catheter is inserted into the ventricle for example via the femoral artery and the aortic arch 3 and carries a series of sensors 4 via which the volume can be determined. The measurement signals are supplied to a control means or circuit 5. Fluid from the ventricle is withdrawn via a storage vessel 6 and a suction means 7, preferably an external pump. The suction means 7 is cont rolled in a cycled manner as a function of the control signals generated in the control means 5. A catheter 8 is used to return the withdrawn blood to the other border of the artery. Return here takes place preferably during the diastole so that overall correct formation of the augmented pressure waves in the blood vessels is guaranteed.

The volumetric measurement in the ventricle allows differences between the diastolic and systolic volumes to be reliably acquired and the corresponding correction signals for the performance of the cycled pump to be generated. In the control circuit 5 in addition the corresponding fixed values, such as for example a defined cardiac output which is used to control the pump when the measured cardiac output deviates, can be stipulated.

Return via the catheter 8 can take place via a conventional balloon catheter which is occluded and correspondingly cycled so that in fact directed return during the diastole is ensured. The corresponding measured values for the heart rate or for the correct instant of the diastole can be obtained from the EKG data. The blood is returned into the central aorta.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An apparatus for supporting performance of the heart in which fluid is taken from blood vessels via a suction catheter and an external suction means and is returned to the blood vessels via a return catheter, the amount of fluid being controlled as a function of measured values, the apparatus comprising at least one sensor for measuring the volume of fluid per unit of time; said at least one sensor connected to an evaluation circuit in which a ratio of diastolic volume to systolic volume per unit of time is evaluated and a corresponding signal generated; and control means for controlling said external suction means as a function of said generated signal.

2. The apparatus of claim 1, wherein said at least one sensor is carried by a suction catheter.

3. The apparatus of claim 2, wherein the suction catheter comprises a cardiac ventricle catheter.

4. The apparatus of claim 2 in further combination with a return catheter adapted to be located in an arterial vessel.

5. The apparatus of claim 1 wherein said control means controls said external suction means such that delivery performance of said external suction means is increased at a low output rate and at low delivery performance of the heart, and is reduced at correspondingly higher measured values.

6. The apparatus of claim 1 wherein said control means controls delivery performance of said external suction means as a function of measured values for the output rate so as to achieve an output rate between 65 and 80%.

7. The apparatus of claim 1 wherein suction performance of said external suction means is accomplished depending on computed and measured cardiac output such that said external suction means delivers fluid based on a difference between computed cardiac output and the measured volume per unit of time.

8. The apparatus of claim 1 wherein said external suction means is controlled as a discontinuously cycled pump.

9. The apparatus of claim 8, wherein a cycle of said pump is fixed or is synchronized to the heartbeat.

10. The apparatus of claim 9, wherein return of the fluid is achieved by adjusting the cycle of said discontinuously cycled pump means.

11. The apparatus of claim 1 wherein said suction means comprises a controllable external pump.

12. The apparatus of claim 1 wherein blood removed from the heart is removed volumetrically by said external suction means, enriched with $O_2$ in a oxygen generator, and returned to circulation.

13. The apparatus of claim 1 wherein said evaluation circuit evaluates the output rate and/or the deviation of the volume that has been delivered to the heart per unit time from a defined setpoint.

14. The apparatus of claim 13 wherein said defined setpoint is computed from body-specific data for the cardiac output.

* * * * *